United States Patent
Mori et al.

(10) Patent No.: US 6,547,741 B2
(45) Date of Patent: *Apr. 15, 2003

(54) WRIST SPHYGMOMANOMETER

(75) Inventors: Kentaro Mori, Shimogyo-ku (JP); Takahide Tanaka, Shimogyo-ku (JP); Akira Nakagawa, Shimogyo-ku (JP); Iwao Kojima, Shimogyo-ku (JP)

(73) Assignee: Omron Corporation, Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/977,383

(22) Filed: Oct. 16, 2001

(65) Prior Publication Data

US 2002/0019592 A1 Feb. 14, 2002

Related U.S. Application Data

(62) Division of application No. 09/582,985, filed on Jul. 10, 2000, now Pat. No. 6,379,310, which is a continuation of application No. PCT/JP99/00082, filed on Jan. 13, 1999.

(30) Foreign Application Priority Data

Jan. 13, 1998 (JP) ............................................. 10-4528
Jan. 14, 1998 (JP) ............................................. 10-5278

(51) Int. Cl.$^7$ ................................................. A61B 5/02
(52) U.S. Cl. ...................... 600/490; 600/500; 600/485; 600/503
(58) Field of Search .................................... 600/485, 490, 600/493–496, 500–3

(56) References Cited

U.S. PATENT DOCUMENTS

| 5,094,293 | A | 3/1992 | Shinmura |
| 5,505,207 | A | 4/1996 | Abbs et al. |
| 5,778,879 | A | 7/1998 | Ota et al. |
| 5,906,582 | A | 5/1999 | Kondo et al. |

FOREIGN PATENT DOCUMENTS

| JP | 58-209334 | 12/1983 |
| JP | 61-193635 | 8/1986 |
| JP | 62-180869 | 11/1987 |
| JP | 64-29768 | 2/1989 |
| JP | 1-265939 | 10/1989 |
| JP | 3-221030 | 9/1991 |
| JP | 5-11902 | 2/1993 |
| JP | 7-275213 | 10/1995 |
| JP | 9-285453 | 11/1997 |

*Primary Examiner*—Robert L. Nasser
(74) *Attorney, Agent, or Firm*—Morrison & Foerster LLP

(57) ABSTRACT

A sphygmomanometer includes a body 10 and a cuff 20 which is integrally attached to the body 10 and wrapped around the wrist. The body 10 is attached to the cuff 20 such that the body is located on the thumb side of the arm L when the sphygmomanometer is fitted on the wrist. Consequently, a precise blood pressure measurement and precise blood pressure fluctuation can be obtained without restriction on the location where the blood pressure measurement is conducted.

8 Claims, 8 Drawing Sheets

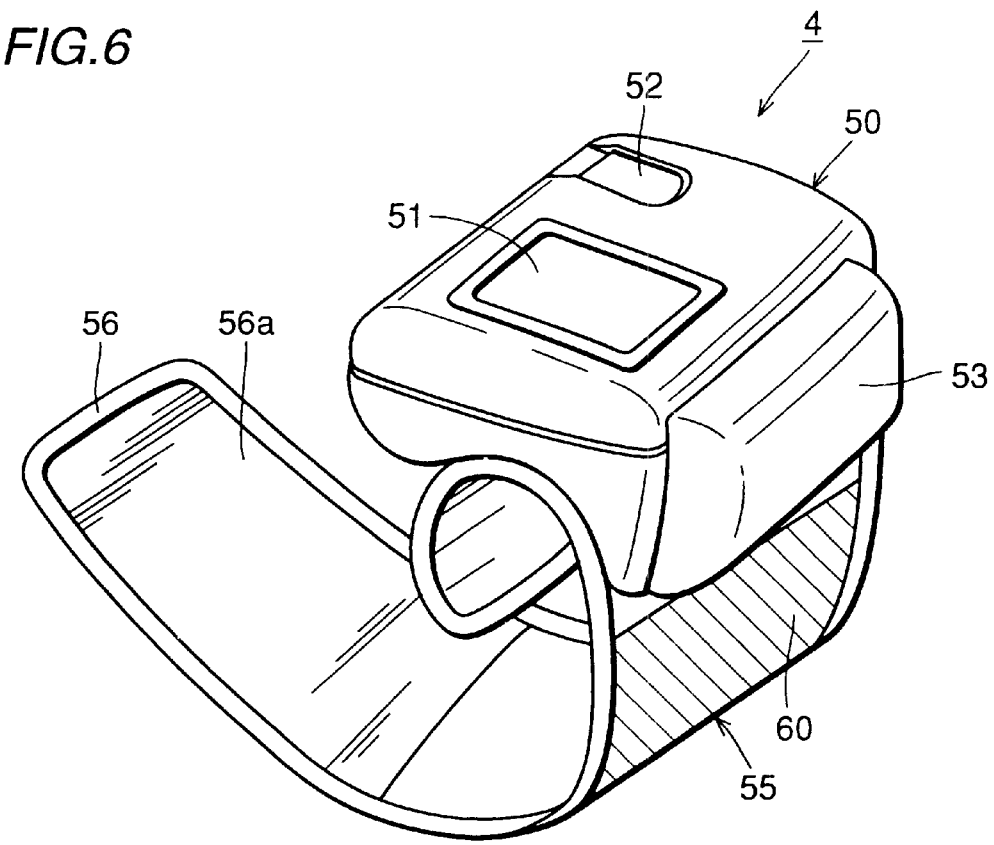

*FIG.9*
PRIOR ART
*FIG.10*
PRIOR ART
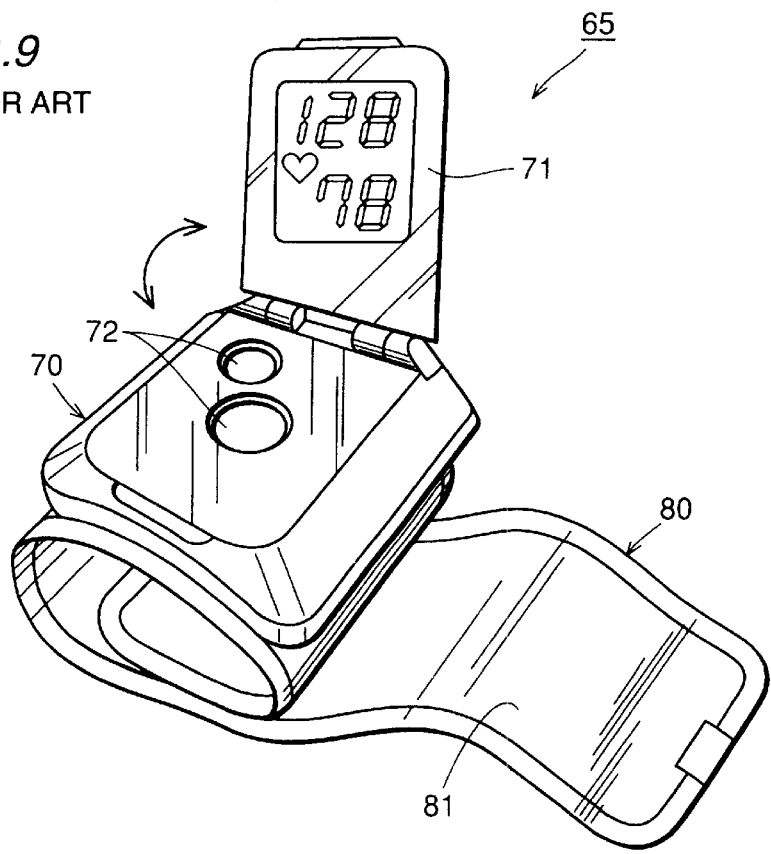
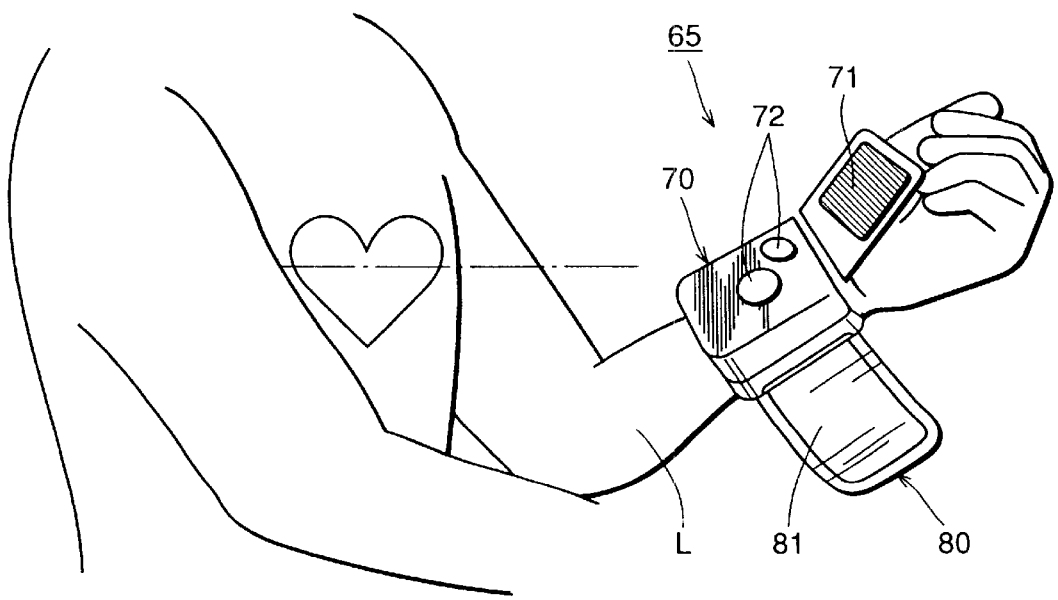

WRIST SPHYGMOMANOMETER

This application is a division of Ser. No. 09/582,985, filed Jul. 10, 2000, now U.S. Pat. No. 6,379,310.

TECHNICAL FIELD

The present invention relates to a wrist sphygmomanometer for measuring blood pressure by wrapping a cuff around the wrist to pressurize the wrist.

BACKGROUND ART

One example of conventional wrist sphygmomanometers of this type is shown in FIG. 9. A wrist sphygmomanometer 65 includes a body 70 and a cuff 80 which is integrally attached to body 70 and wrapped around the wrist. Body 70 has a display unit 71 which can stand up to display blood pressure measurements (maximum and minimum blood pressures), pulse rate and the like, and an operation unit 72 for a power ON/OFF (measurement start/stop) switch and the like. Cuff 80 contains therein a curler (not shown) for elastically maintaining cuff 80 in a substantially circular shape, and the curler is provided inside a cuff band 81 having on its surface a hook-and-loop fastener.

As shown in FIG. 10, sphygmomanometer 65 requires that cuff 80 is wrapped around the wrist of the left arm L, for example, with body 70 located on the inside (palm side) of left arm L and that the site of measurement (wrist) is matched in height with the heart (represented by the heart-shaped symbol) in order to accurately measure the blood pressure.

The conventional sphygmomanometer 65 described above requires the posture for measurement as shown in FIG. 10. Therefore, in use of sphygmomanometer 65, measurement is desirably conducted in the condition that the user sits on a chair or the like with the elbow rested on a table or the like, the measurement site (wrist) and the heart are matched in height, and the left arm is placed on an armrest such as a cushion in order to stabilize the measurement site.

However, there is a certain distance between the chest and the measurement site of the user in this posture so that it is difficult to match the height of the measurement site with that of the heart. A resultant problem is difficulty in obtaining a precise measurement of blood pressure. In addition, each time the blood pressure is measured, the height of the measurement site is likely to vary, causing an error of the blood pressure measurement due to the varying height of the measurement site and accordingly causing a problem that an accurate fluctuation of the blood pressure (blood pressure variation) is difficult to know. Another problem is that the location for measuring the blood pressure is restricted because of the need for an armrest for stabilizing the arm as well as a desk or the like on which the elbow is rested, in order to allow the user to take the posture illustrated above.

FIG. 11 shows another example of the conventional wrist sphygmomanometers. A sphygmomanometer 66 shown in FIG. 11 is similar to that shown in FIG. 9 in that the former includes a body 74 and a cuff 84 which is integrally attached to body 74 and wrapped around the wrist. Body 74 of sphygmomanometer 66 also has a display unit 76 for indicating blood pressure measurements (maximum and minimum blood pressures), pulse rate and the like and an operation unit 77 for a power ON/OFF (measurement start/stop) switch and the like.

Sphygmomanometer 66 is used by wrapping cuff 84 around the wrist of the left arm with body 74 located on the inner side (palm side) of the left arm, for example. When cuff 84 (i.e. air bag) is inflated for measurement of blood pressure, cuff 84 pressurizes the inner side of the left arm. In order to prevent the air bag from expanding outward (toward body 74), body 74 has its surface (back side) facing cuff 84, that is formed into C-shape (recessed) according to the curve of the corresponding opposite portion of cuff 84.

In order to realize a posture for measurement for allowing body 74 to be located on the inner side of the left arm, some heavy loads (mainly battery, motor, pump and the like) are arranged in sections 75a and 75b with the boundary represented by the dotted line in FIG. 11 such that the weights of the loads are balanced. Then, the fitness of sphygmomanometer 66 to the wrist is improved.

Sphygmomanometer 66 shown in FIG. 11 also requires that the measurement site (wrist) is matched with the heart in height for accurate measurement of blood pressure, and accordingly the wrist is placed lightly on the chest for measurement. This posture for measurement leads to a problem that sphygmomanometer 66 of this type cannot be reduced in size. Specifically, if the width of body 74 in the direction of extension of cuff 84 is decreased in order to avoid the side face of body 74 on the palm side from heavily pressing the chest, it would be difficult to balance the heavy loads in body 74. Further, body 74 would become unstable on the inner side of the left arm, resulting in deteriorated fitness.

Since heavy internal components are arranged within body 74 with their weights well-balanced, body 74 fitted on the wrist (the cuff has not been wrapped therearound which means that the body is just put on the wrist) sits on the wrist in a stable manner. However, when cuff 84 is being wrapped around the wrist, one end of cuff 84 is pulled so that body 74 is likely to shift from its original position on the wrist. Consequently, body 74 which was balanced is going to turn along the wrist and the weight balance is lost. When cuff 84 is actually wrapped around the wrist, body 74 could be shifted from the original desired position and attached as it is to the wrist. Therefore, the attachment is troublesome because the wrapping must be done carefully.

The present invention is made to address these problems. One object of the invention is to provide a wrist sphygmomanometer which is easier to handle.

Another object of the invention is to provide a wrist sphygmomanometer to enable an accurate blood pressure measurement and an accurate blood pressure fluctuation to be obtained without restriction on the location for measuring blood pressure.

Still another object of the invention is to provide a wrist sphygmomanometer of a smaller size which is easily attached.

DISCLOSURE OF THE INVENTION

In order to achieve the objects above, a wrist sphygmomanometer according to the present invention includes a body and a cuff which is integrally attached to the body and wrapped around a wrist. The body is attached to the cuff such that the body is located on thumb side of the arm when the sphygmomanometer is fitted on the wrist.

When this sphygmomanometer is fitted on the wrist with its cuff wrapped around the wrist, the body is located on the thumb side of the arm, while the conventional sphygmomanometer has its body located on the inner side (palm side) of the arm. Therefore, the sphygmomanometer of the invention allows a measurement site (wrist) to be placed on the chest for measuring blood pressure. As a result, the distance between the measurement site and the chest becomes shorter, and the height of the measurement site can easily be matched with that of the chest. Precise measurement of blood pressure is thus possible. In addition, since there are fewer instances in which the height of the measurement site varies each time blood pressure is measured, the fluctuation of blood pressure can accurately be known. Further, since the posture can be realized such that the measurement site is placed on the chest, the armrest, table on which the elbow is rested, and the like are unnecessary and thus the location for measuring blood pressure is less limited. As a result, it is possible to provide a wrist sphygmomanometer which is easier to handle and which can take an accurate blood pressure measurement as well as a precise blood pressure fluctuation without limitation on the location for measuring blood pressure.

According to another aspect of the invention, a wrist sphygmomanometer includes a body having a power supply housing portion and a cuff which is integrally attached to the body and wrapped around a wrist. The body is attached to the cuff such that the body is located on thumb side of the arm when the sphygmomanometer is fitted on the wrist. The power supply housing portion is provided to the body such that the housing portion houses power supply in the direction perpendicular to the body when the body is substantially kept horizontally.

When this sphygmomanometer is fitted on the wrist with the cuff wrapped around the wrist, the body is located on the thumb side of the arm, while the conventional sphygmomanometer has its body located on the inner side (palm side) of the arm, and accordingly the sphygmomanometer of the invention can be reduced in size. Specifically, since the body can be less protruded on the palm side (inner side), the inner side of the body never strongly presses the chest even if the measurement site (wrist) is placed on the chest. Further, since the power supply housing portion is provided to the body such that the housing portion houses the power supply in the direction vertical to the body, stability of the body is enhanced when the sphygmomanometer is fitted on the wrist and accordingly the fitness is improved.

According to still another aspect of the invention, a wrist sphygmomanometer includes a body and a cuff which is integrally attached to the body and wrapped around a wrist. The body is attached to the cuff such that the body is located on thumb side of the arm or on the outer side of the arm corresponding to back of hand. The cuff has on its palm side surface an indication-and-block member for preventing the cuff from inflating outward.

According to a further aspect of the invention, a wrist sphygmomanometer includes a body and a cuff which is connected to the body via an air flow passage member and wrapped around a wrist. The cuff has on its palm side surface an indication-and-block member for preventing the cuff from inflating outward.

When the cuff of these wrist sphygmomanometers is wrapped around the wrist, the indication-and-block member is located on the palm side surface (inner side of the arm corresponding to the palm side) to prevent the cuff from expanding outward.

BRIEF DESCRIPTION OF THE DRAWINGS

FIG. 6 is a perspective view of a wrist sphygmomanometer according to a further embodiment of the invention.

FIG. 9 is a perspective view of a conventional wrist sphygmomanometer.

FIG. 10 shows a posture for measurement with the conventional wrist sphygmomanometer shown in FIG. 9 fitted on the wrist of left arm.

BEST MODES FOR CARRYING OUT THE INVENTION

The present invention will be described in more detail in conjunction with the attached drawings.

(1) First Embodiment

Figure 1:
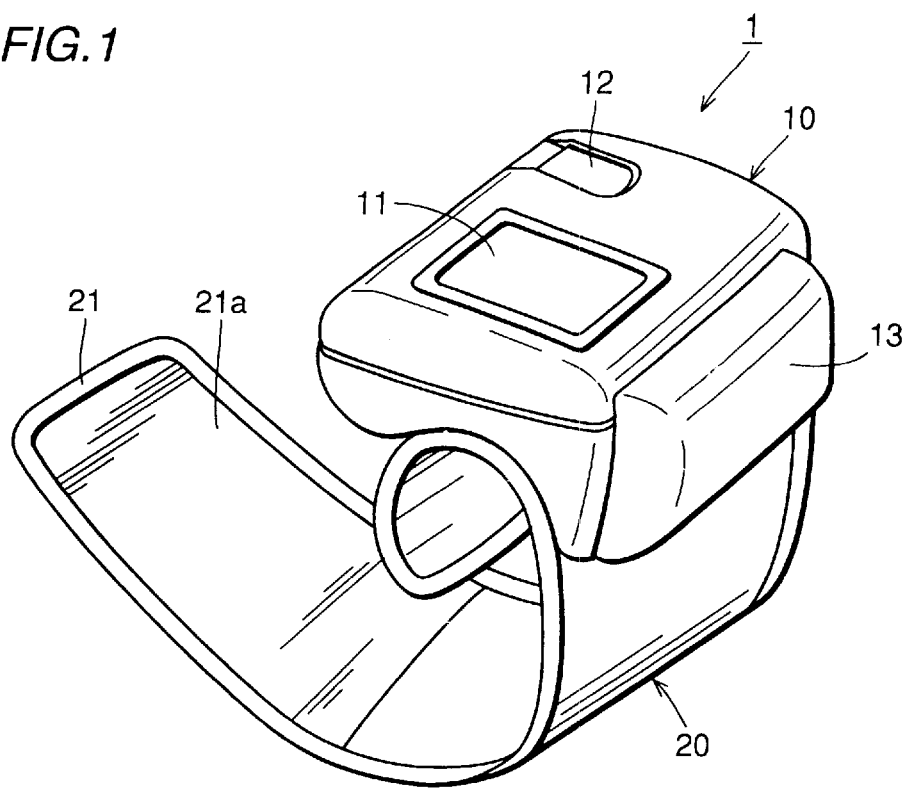
FIG. 1 is a perspective view of a wrist sphygmomanometer according to one embodiment of the invention.

Referring to FIG. 1 which is a perspective view of a wrist sphygmomanometer 1 according to the first embodiment of the invention, wrist sphygmomanometer 1 includes a body 10 and a cuff 20 which is integrally attached to body 10 and wrapped around the wrist. Body 10 has its back side (the side which faces cuff 20) curved to form a recess according to the shape of cuff 20. Body 10 includes a display unit 11 for displaying icon or the like which indicates blood pressure measurements (maximum and minimum blood pressures), pulse rate, and operation sequence of the sphygmomanometer, an operation unit 12 having a switching function to turn on/off the power and start pressurization of cuff 20, and a battery cover 13 which is detachable for allowing a battery to be loaded/unloaded. Display unit 11 and operation unit 12 are arranged on a front side (opposite to the curved back side) of body 10 and battery cover 13 is arranged on an inner side of body 10. Body 10 further includes therein components (not shown) which are a pump for sending air into cuff 20, a pressure sensor for detecting the pressure in cuff 20, a discharge valve for discharging air from cuff 20, a battery portion for housing a battery, and a circuit board on which various electronic components are mounted.

Cuff 20 includes therein a curler (not shown) in an elliptical shape for elastically maintaining cuff 20 in the shape of ellipse, and the curler is provided within a cuff band 21 having on its surface a hook-and-loop fastener 21a. As seen from FIG. 1, body 10 is attached to the portion where the curvature of the elliptical curler (i.e. elliptical portion of cuff 20) is the maximum one (attached to the major axis portion of the ellipse). Since cuff 20 is shaped into the ellipse and body 10 is attached to the major axis portion of elliptical cuff 20, the user can assume a posture to allow the wrist, on which sphygmomanometer 1 is fitted for taking measurement, to be placed on the chest as described below.

Figure 2:
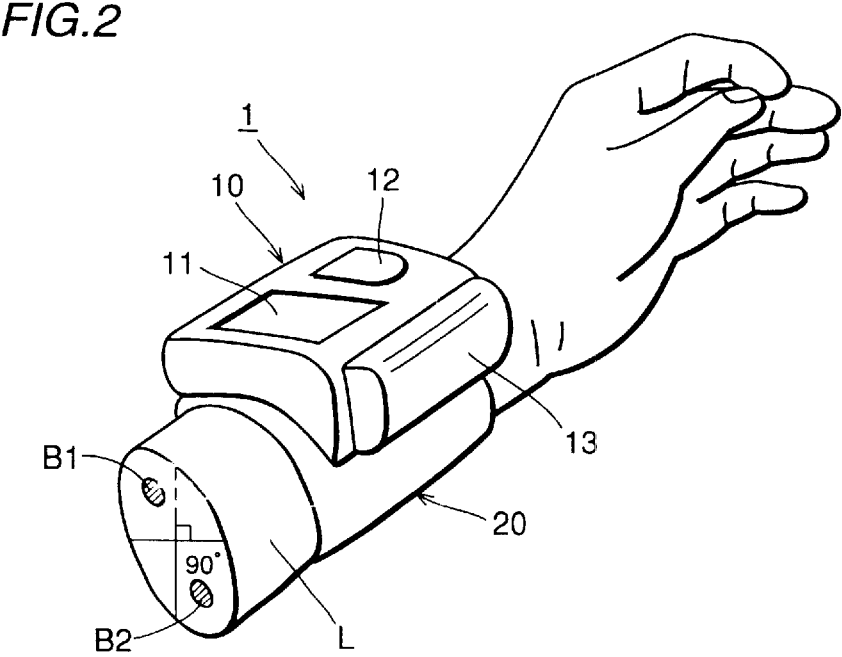
FIG. 2 shows the sphygmomanometer shown in FIG. 1 which is fitted on the wrist of left arm.

Sphygmomanometer 1 described above is fitted on the wrist of left arm L, for example, as shown in FIG. 2. Specifically, in accordance with the substantially elliptical cross section of the left arm (right arm also has the elliptical cross section) of the human body, the corresponding elliptical portion of cuff 20 is fitted on the side (on the thumb side) of left arm L, cuff 20 is then wrapped around the wrist, and hook-and-loop fastener 21a of cuff band 21 is used to fasten cuff 20 to the wrist. When sphygmomanometer 1 is fitted on the wrist, body 10 is located on the side (thumb side) of left arm L. In this state of fitting, display unit 11 and operation unit 12 are located on the side of left arm L according to the arrangement of body 10. In other words, body 10 is located on the radius B1, corresponding to the thumb side of the arm of the human body while ulna B2 corresponds to the little finger side.

Figure 3:
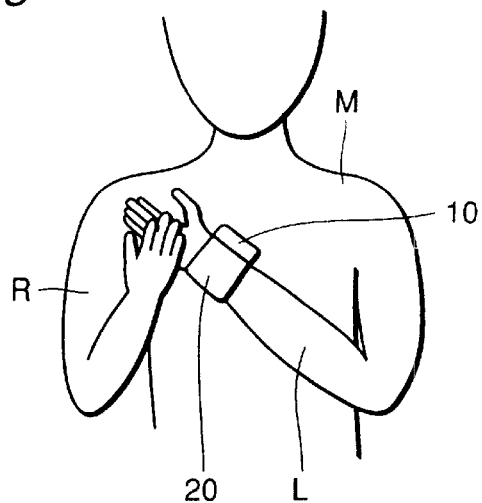
FIG. 3 shows a posture for measurement with the wrist of left arm placed on the chest, the left wrist having the sphygmomanometer fitted thereon.

After sphygmomanometer 1 is fitted on the wrist of left arm L, the user assumes a posture for measurement as shown in FIG. 3 such that the measured site (wrist) is placed on the chest at the height substantially equal to that of the heart. At this time, the right hand may support the left hand to ease the load. Even when this posture is taken, display unit 11 and operation unit 12 of sphygmomanometer 1 are located on the side of body 10, i.e., on the thumb side of left arm L. Therefore, indication on display unit 11 is easy to see, and an operation for turning on/off the power and starting pressurization by using operation unit 12 is also easy.

Further, since blood pressure can be measured with this posture shown in FIG. 3, the distance between the measured site and the chest is shortened and the height of the measured site can easily be matched with that of the heart. In addition, there are fewer instances in which the height of the measured site varies each time blood pressure is measured. Accordingly, blood pressure can be measured accurately and the fluctuation of the blood pressure can precisely be known. There is no need for armrest, table on which elbow is rested, and the like, and restriction on the location for measuring blood pressure is thus relieved.

The body of the conventional sphygmomanometer 65 (see FIGS. 9 and 10) is located on the inner side of left arm L, while body 10 is attached to the major axis portion of the elliptical cuff 20 and the back side of body 10 coupled to cuff 20 is shaped in accordance with cuff 20. Therefore, the space for housing internal components (especially power supply) can be secured in the vertical direction of body 10. Specifically, in this embodiment, the battery portion is arranged on the palm side (inner side) of body 10 in order to house two batteries aligned in the vertical direction. In this way, the width of body 10 in the direction in which cuff 20 extends (circumferential direction of the wrist) can be decreased and accordingly the sphygmomanometer can be reduced in size so that the portability can be improved. As a comparison, the conventional sphygmomanometer 65 as shown in FIG. 9 has body 70 positioned on the inner side of the arm (see FIG. 10) and is thus limited regarding the width of body 70 in the direction of extension of cuff 80. Therefore, the conventional sphygmomanometer cannot be reduced in size for enhancement of the portability.

(2) Second Embodiment

Figure 4A:
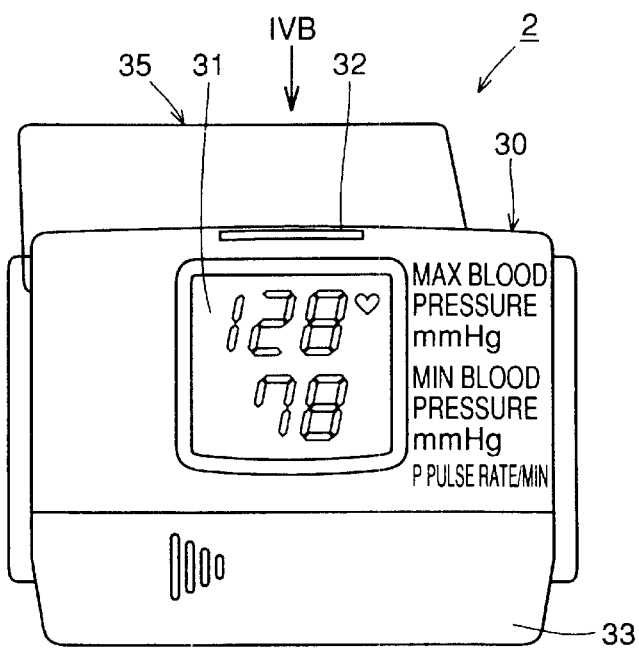
FIG. 4A is a plan view of a wrist sphygmomanometer in another embodiment.
Figure 4B:
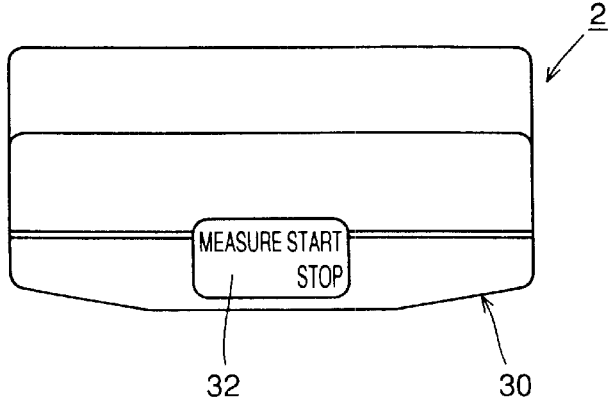
FIG. 4B shows a side thereof viewed in the direction of the arrow IVB.

A wrist sphygmomanometer 2 according to the second embodiment is shown in FIGS. 4A and 4B. It is noted that a cuff 35 is not shown in FIG. 4B. Wrist sphygmomanometer 2, which is similar to sphygmomanometer 1 described above in the basic structure, is also constituted of a body 30 and cuff 35. Sphygmomanometer 2 has a display unit 31 arranged at the center of the front side of body 30 and an operation unit 32 arranged at the center of an outer side (the side corresponding to the back of hand) of body 30. A battery cover 33 is of slide type.

When sphygmomanometer 2 is fitted on the wrist, operation unit 32 is located on the side corresponding to the back of the hand, so that operation unit 32 is easy to operate. This sphygmomanometer also achieves the functional effects similar to those discussed above. In particular, since this sphygmomanometer has display unit 31 and operation unit 32 positioned at the central part of body 30, display 31 is easy to watch and operational easiness of operation unit 32 is maintained regardless of the location, i.e., left arm or right arm, where the sphygmomanometer is fitted. Therefore, the sphygmomanometer can be used on any arm, whether the subject is right-handed or left-handed.

(3) Third Embodiment

Figure 5A:
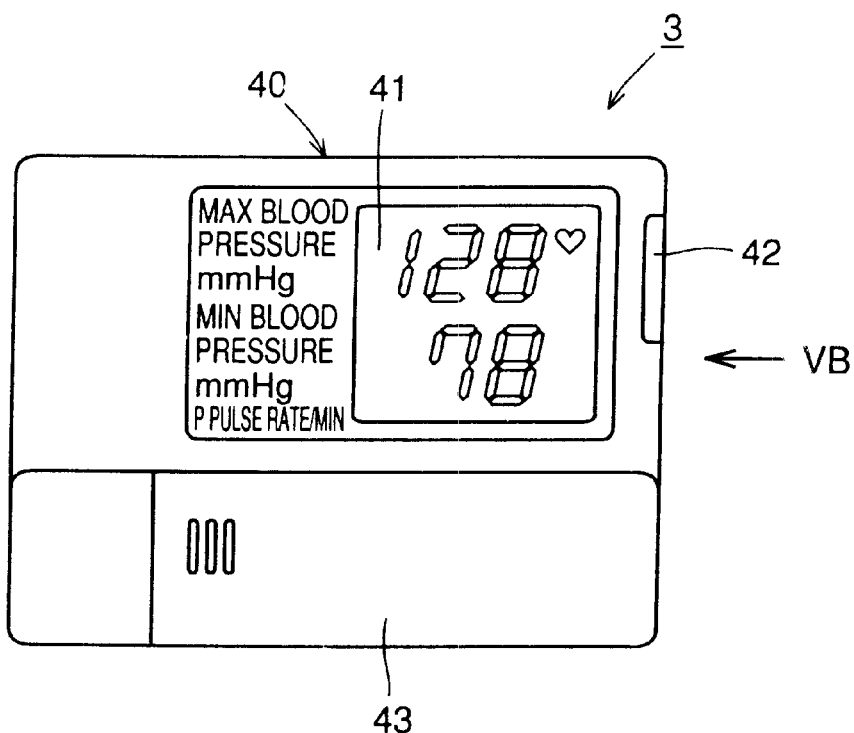
FIG. 5A is a plan view of a wrist sphygmomanometer in still another embodiment.
Figure 5B:
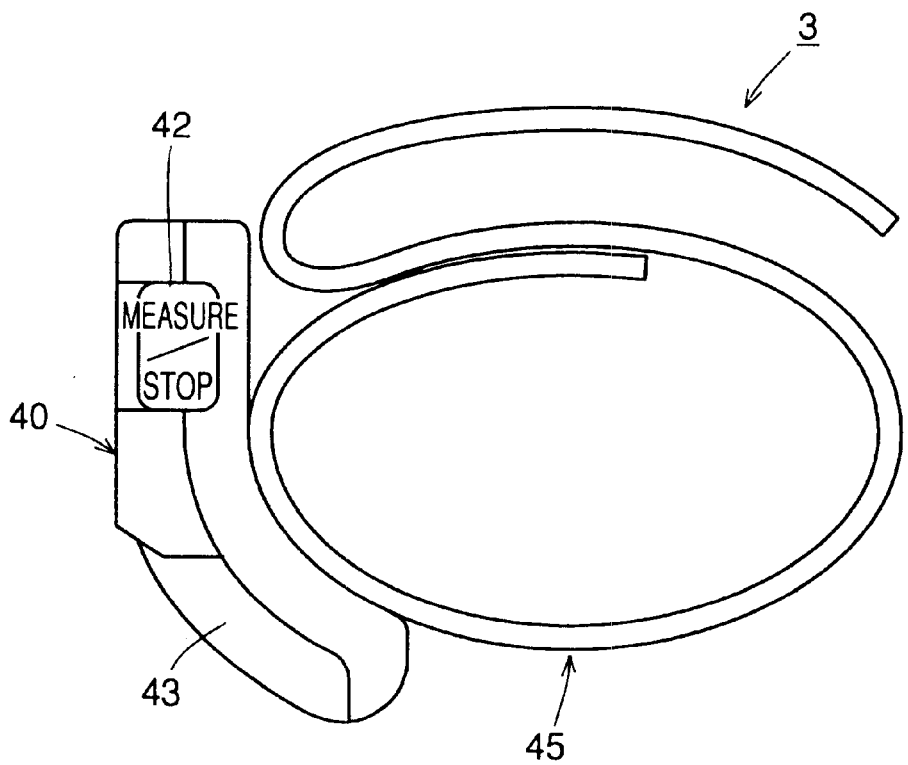
FIG. 5B shows a side thereof viewed in the direction of the arrow VB.

A wrist sphygmomanometer 3 according to the third embodiment is shown in FIGS. 5A and 5B. It is noted that a cuff 45 is not shown in FIG. 5A. As described above, wrist sphygmomanometer 3 is also constituted of a body 40 and cuff 45. Sphygmomanometer 3 has a display unit 41 arranged on the front side of body 40 and an operation unit 42 arranged on a side in the lateral direction of body 40 (right side in this example). A battery cover 43 is of slide type.

When sphygmomanometer 3 is fitted on the wrist, operation unit 42 is located on the side corresponding to the thumb (when the sphygmomanometer is fitted on the wrist of left arm). Therefore, operation unit 42 is easy to operate. Sphygmomanometer 3 also has functional effects similar to those discussed above.

In addition to the arrangements of the first to the third embodiments, an arrangement may be possible which allows both of the display and operation units to be located on a side of the body corresponding to the back of the hand (on the outer side of the body). Specifically, this arrangement corresponds to that in the second embodiment shown in FIG. 4 in which not only operation unit 32 but also display unit 31 is arranged on the outer side of body 30. However, preferably the outer side of body 30 is extended to the extent which does not disturb cuff 35 to secure the space for placing display unit 41.

(4) Fourth Embodiment

Figure 7:
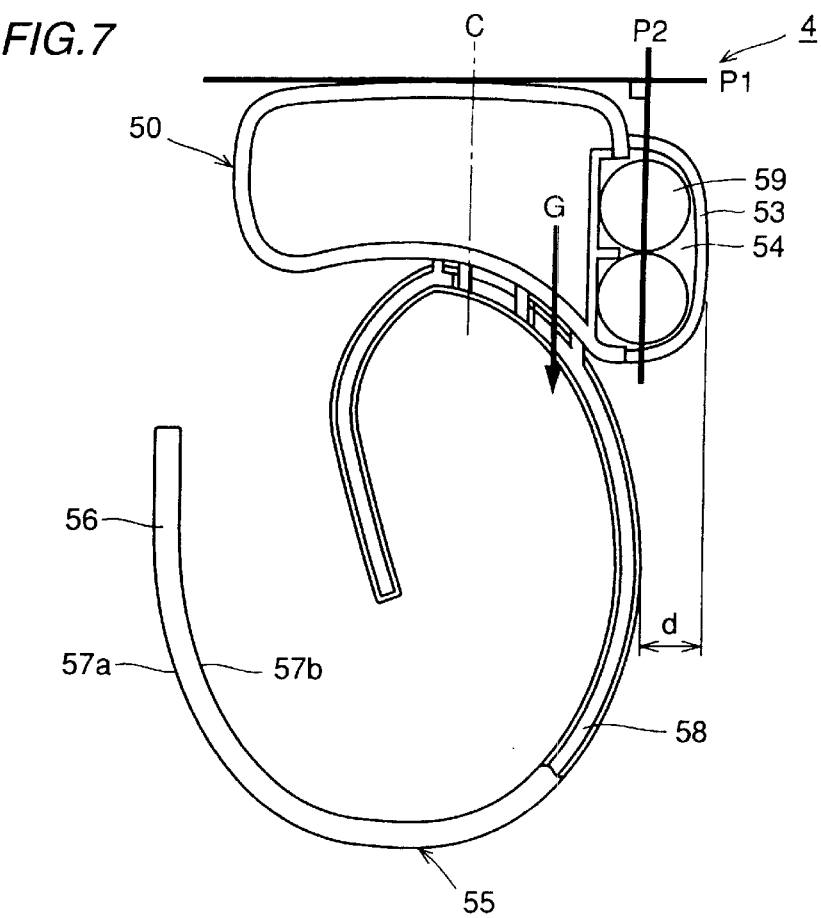
FIG. 7 is a cross sectional view of the sphygmomanometer shown in FIG. 6.

FIG. 6 is a perspective view of a wrist sphygmomanometer 4 according to the fourth embodiment and FIG. 7 is a cross sectional view thereof Similarly to the sphygmomanometers in the embodiments above, sphygmomanometer 4 according to the fourth embodiment includes a body 50 and a cuff 55 which is integrally attached to body 50 and wrapped around the wrist. Body 50 has its back side (the side corresponding to cuff 55) which is curved to form a recess in accordance with the shape of cuff 55. Body 50 includes a display unit 51 for displaying an icon or the like to indicate blood pressure measurements (maximum and minimum blood pressures), pulse rate, and operation sequence of the sphygmomanometer, an operation unit 52 having a switching function to turn on/off the power and start pressurization of cuff 55, and a detachable battery cover 53 to allow a battery 59 to be loaded/unloaded. Display unit 51 and operation unit 52 are arranged on the front side (opposite to the curved back side), and battery cover 53 is attached to cover a power supply housing portion 54 provided on the inner side of body 50. Body 50 further includes therein the components (not shown) which are a pump for sending air into cuff 55, a pressure sensor for detecting pressure in cuff 55, a discharge valve for discharging air from cuff 55, and a circuit board on which various electronic components are mounted.

Cuff 55 has a cuff band 56, an elastic air bag (formed of rubber, for example, not clearly shown in FIG. 7) is provided between an outer sheet 57a and an inner sheet 57b constituting cuff band 56, and an elastic curler 58 which can be curved is arranged between the air bag and outer sheet 57a. Further, hook and loop fasteners 56a (see FIG. 6) are provided respectively on appropriate portions of the respective surfaces of outer sheet 57a and inner sheet 57b of cuff band 56 in order to fasten cuff 55 to the wrist.

Cuff 55 further has an indication-and-block member 60 on its surface corresponding to the palm for preventing cuff 55 from expanding outward (see FIG. 6). On indication-and-block member 60, directions for using sphygmomanometer 4 are briefly indicated together with the type and the like thereof. Block member 60 is not limited to a particular one if it can hinder the air bag from inflating outward. For example, a transparent sheet having an appropriate rigidity may be welded or sewn to a proper portion of cuff 55 (outer sheet 57a of cuff band 56), or only a proper portion of cuff band 56 may be increased in thickness, or another curler may be provided in addition to curler 58 within cuff 55. Block member 60 thus provided enables body 50 to be attached freely to cuff 55. As a comparison, a conventional sphygmomanometer 66 as shown in FIG. 10 has a body 70 which prevents a cuff 80 from expanding outward as discussed above. In this case, the location where body 70 is attached to cuff 80 is restricted.

Body 50 is attached to the portion of elliptical curler (i.e., elliptical portion of cuff 55) where the curvature thereof is the maximum one (attached to the major axis portion of the ellipse). It is noted that body 50 and cuff 55 are coupled by engaging an engagement hook protruding from curler 58 with an angled hole formed in body 50. Since cuff 55 is formed in the shape of ellipse and body 50 is attached to the major axis portion of elliptical cuff 55, the width of body 50 in the direction of extension of cuff 55 can be reduced and accordingly sphygmomanometer 4 can be decreased in size.

Specifically, referring to FIG. 7, body 50 is attached by cuff 55 such that body 50 is located on the thumb side of the arm when sphygmomanometer 4 is fitted on the wrist, and power supply housing portion 54 is arranged between the palm side (inner side) of body 50 and the center C of body 50 with respect to the direction of extension of cuff 55 for housing two batteries 59 in the vertical direction. In other words, in order to effectively utilize the space extending from the major axis to the minor axis of elliptical curler 58, the cross section of body 50 including power supply housing portion 54 is formed substantially into the L-shape. Then, body 50 including power supply housing portion 54 can be reduced in size.

In this embodiment, plane P1 meeting the top of the front side of body 50 is perpendicular to plane P2 crossing the centers of batteries 59 within power supply housing portion 54, and the center of gravity G of body 50 including batteries 59 is positioned between the center C of body 50 and the palm side thereof. Further, the plane meeting the top of the palm side of power supply housing portion 54 (i.e. battery cover 53) is substantially set at the same level as that of the plane meeting the top of the palm side of cuff 55 leaving only a distance d of about 2 to 3 mm.

Sphygmomanometer 4 described above is fitted on the wrist of left arm L, for example, similarly to the first embodiment as shown in FIG. 2. Specifically, in accordance with the substantially elliptical cross section of the left arm (or right arm) of the human body, the elliptical portion of cuff 55 is fitted on the side (thumb side) of left arm L, cuff 55 is then wrapped around the wrist, and hook-and-loop fastener 56a of cuff band 56 is used to fasten cuff 55 to the wrist. When sphygmomanometer 4 is fitted on the wrist, body 50 is located on the side (corresponding to the thumb of left hand) of left arm L. In other words, body 10 is located on radius B1 of the arm of the human body corresponding to the thumb side while ulna B2 is located on the little finger side. Power supply housing portion 54 is located on the palm side and block member 60 of cuff 55 is located on the inner side of left arm L.

As discussed above, the center of gravity G of body 50 is positioned between the center C of body 50 and the palm side (inner side) thereof. Therefore, when cuff 55 is fitted on the side of left arm L, the palm side of body 50 is surely supported on the wrist. Specifically, regarding sphygmomanometer 4 in this embodiment, body 50 is put on the wrist in a condition that the weight balance is lost from the beginning (body is fitted on the wrist with heavy loads such as power supply intentionally arranged on one end of the body). At this time, the elasticity of the curler which is included within cuff 55 and shaped in accordance with the wrist and the frictional force between the surface of the cuff contacting the wrist and the surface of the skin of the wrist cause cuff 55 to be tightened slightly around the wrist when the cuff is temporarily fitted on the wrist. Accordingly, when cuff 55 is being wrapped around the wrist, even if one end of the cuff is pulled, body 50 is less likely to be shifted from the original position in the temporal fitting. As a result, cuff 55 can easily be wrapped around the wrist while body 50 is positioned on the side of left arm L and the fitness is thus improved.

After the sphygmomanometer is fitted on the wrist of left arm L, a posture is taken such that the measured site (wrist) is placed on the chest substantially at the same height as that of the heart in a similar manner to that of the embodiment above as shown in FIG. 3. At this time, comfortability is enhanced by supporting the left hand with the right hand. Even when this posture is assumed, the top of the palm side of power supply housing portion 54 is substantially at the same level as the top of the palm side of cuff 55 (power supply housing portion 54 is not so conspicuously protruded toward the palm side). Therefore, power supply housing portion 54 does not strongly press the chest and body 50 never rotates to shift from the original position. Although cuff 55 (air bag) is inflated for measuring blood pressure and accordingly cuff 55 expands inward to pressurize the inner side of left arm L, cuff 55 does not expand outward because of the presence of block member 60 on the inner side of left arm L. Therefore, cuff 55 is efficiently inflated by the air supplied into the air bag.

Figure 8A:
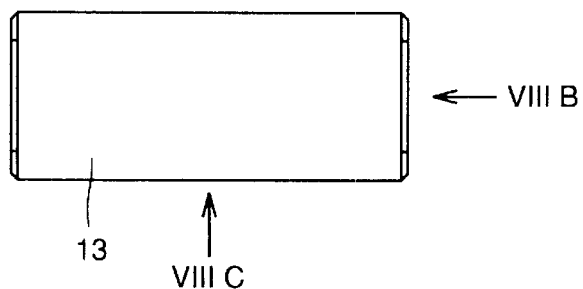
FIG. 8A is a plan view of a battery cover detachably attached to a power supply housing portion of a body of the sphygmomanometer shown in FIG. 6.
Figure 8B:
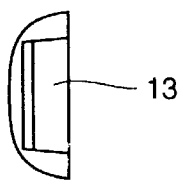
FIG. 8B shows a side thereof viewed in the direction of the arrow VIIIB in FIG. 8A.
Figure 8C:
FIG. 8C shows a side thereof viewed in the direction of the arrow VIIIC in FIG. 8A.
Figure 11:
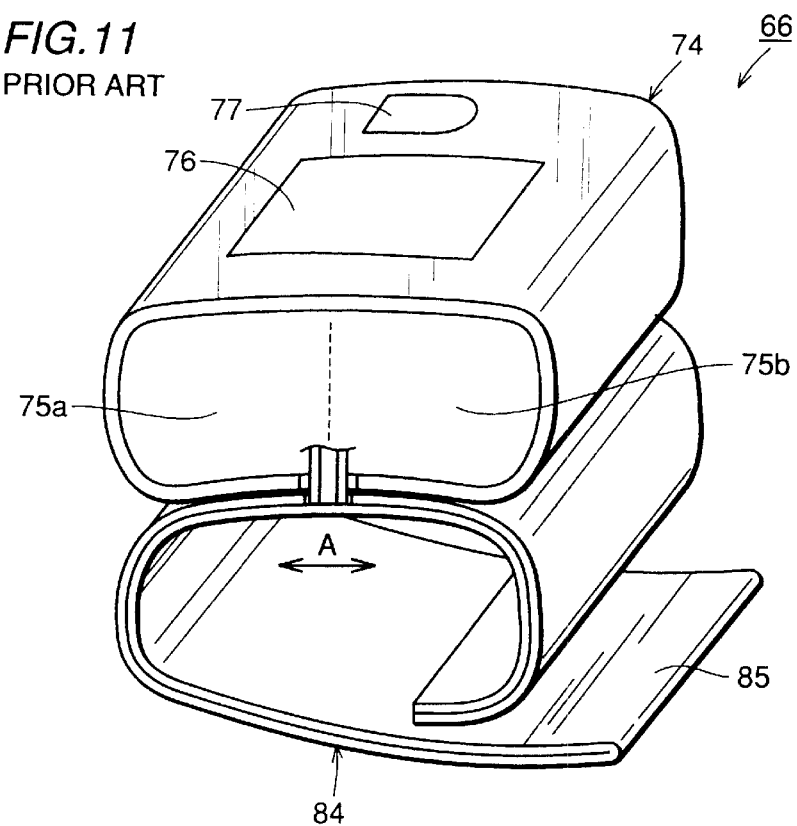
FIG. 11 is a perspective view of a conventional wrist sphygmomanometer with some components omitted.

In this embodiment, battery cover 53 is horizontally and vertically symmetrical in shape as shown in FIGS. 8A, 8B and 8C. Therefore, battery cover 53 can be attached to power supply housing portion 54 in any direction and there is no need to confirm the direction of the attachment. Further, battery cover 53 is attached to or detached from power supply housing portion 54 by being put on/off from the housing, so that attachment/detachment is easy. Battery cover 53 is thus well fitted.

Figure 12:
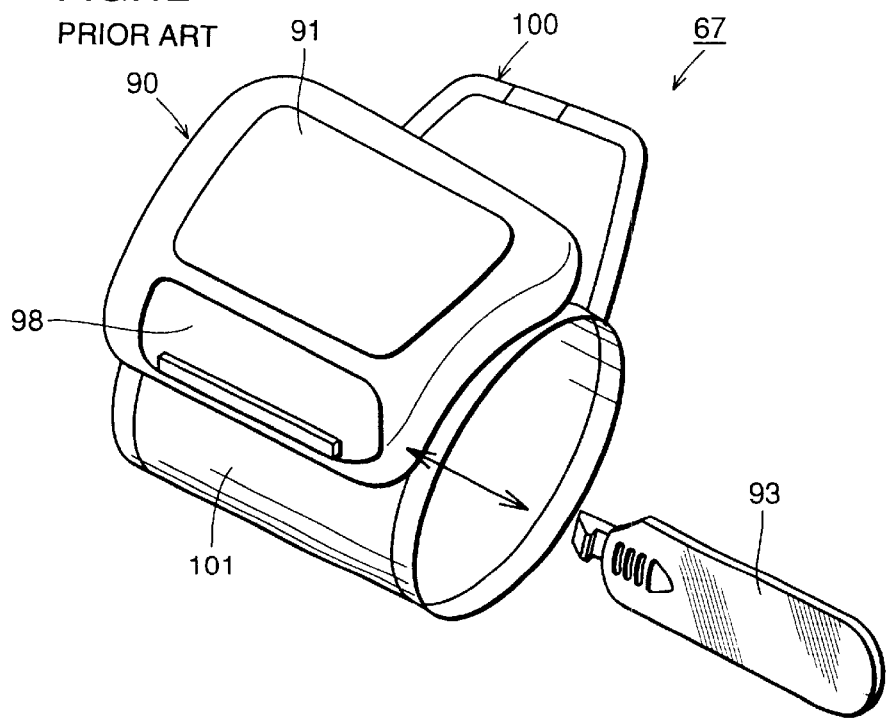
FIG. 12 is a perspective view of another conventional wrist sphygmomanometer.

For comparison, FIG. 12 shows a sphygmomanometer 67 which includes a body 90 having a display unit 91 and a cuff 100 which is integrally attached to body 90 and has a cuff band 101. When a plate-like battery cover 93 is attached to/detached from a power supply housing portion 98 of body 90 in sliding manner, the portion for engagement with the finger is small, which makes sliding of the cover difficult. Therefore, the operation for attachment/detachment cannot be done easily.

Figure 13:
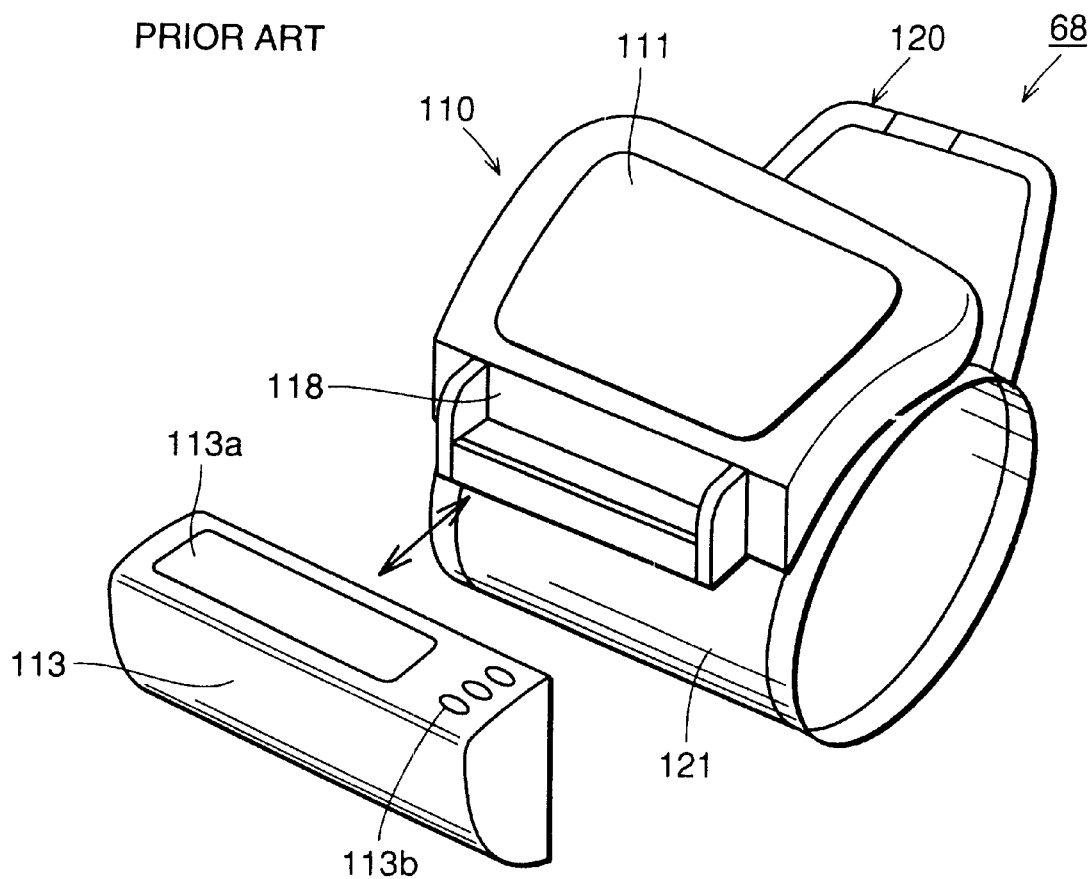
FIG. 13 is a perspective view of still another conventional wrist sphygmomanometer.

FIG. 13 shows a sphygmomanometer 68 which includes a body 110 having a display unit 111 and a cuff 120 which is integrally attached to body 110 and has a cuff band 121. When a battery cover 113 is attached to a power supply housing portion 118 of body 110 by fitting battery cover 113 thereon, battery cover 113 can be fit onto housing portion 118 only in a predetermined direction. In this case, it would be troublesome to confirm the direction, which means the operation for attachment/detachment is not easy. In particular, in order to indicate the direction of attachment of battery cover 113, battery cover 113 may be shaped in a manner to explicitly indicate the horizontal and vertical directions, or a seal 113a or characters 113b may be put on battery cover 113 for indicating the direction. However, an extra space is required to shape the cover into a different form and it will be difficult to reduce the size. Seal and character methods could add the cost.

It is noted that indication-and-block member 60 in the embodiment above is provided to cuff 55 which is integrally attached to allow body 50 of sphygmomanometer 4 fit on the wrist to be located on the thumb side of the arm. However, the surface member on the palm side may be provided in the similar manner to a cuff which is integrally attached to allow body 50 to be located on the side corresponding to the back of hand. Alternatively, the indication-and-block member may be provided similarly to the palm side of the cuff of a sphygmomanometer, which includes a body 50 and a cuff connected to body 50 via an air flow passage member (e.g. tube) and wrapped around the wrist (i.e., the cuff and body are separated).

INDUSTRIAL APPLICABILITY

As heretofore discussed, the sphygmomanometer according to the present invention includes a body which is attached to a cuff such that the body is located on the thumb side of the arm when the sphygmomanometer is fitted on the wrist. Therefore, blood pressure can be measured at a measurement site (wrist) being placed on the chest, and accordingly a sphygmomanometer which is easy to use can be provided.

What is claimed is:

1. A method of measuring blood pressure using a wrist sphygmomanometer including a body and including a cuff attached to the body and wrapped around a wrist, said body being attached to the cuff in a manner to allow the body to be located on a thumb side of an arm when the wrist sphygmomanometer is fitted on the wrist, comprising:

fitting said wrist sphygmomanometer on the wrist;
placing the wrist with said wrist sphygmomanometer fitted thereon on a chest of a subject; and
reading a value detected by said wrist sphygmomanometer with the wrist placed on the chest.

2. The wrist sphygmomanometer of claim 1, further comprising a positioning system which determines whether the sphygmomanometer is at an appropriate measuring level.

3. The wrist sphygmomanometer of claim 2, wherein the positioning system indicates that the sphygmomanometer is at an appropriate measuring level by providing an acoustic signal.

4. The wrist sphygmomanometer of claim 2, further comprising a display that includes arrows which guide a user to the appropriate measuring level.

5. The wrist sphygmomanometer of claim 4, wherein the display indicates that the user has reached the appropriate measuring level by displaying a visual symbol.

6. The wrist sphygmomanometer of claim 4, wherein the display indicates that the user has reached the appropriate measuring level by providing an acoustic signal.

7. The wrist sphygmomanometer of claim 2, wherein a blood pressure measurement is automatically taken when the positioning system determines that the sphygmomanometer is at the appropriate measuring level.

8. A method of measuring blood pressure using a wrist sphygmomanometer including a body and including a cuff attached to the body and wrapped around a wrist, said body being attached to the cuff in a manner to allow the body to be located on a thumb side of an arm when the wrist sphygmomanometer is fitted on the wrist, comprising:

fitting said wrist sphygmomanometer on the wrist;
placing the wrist with said wrist sphygmomanometer fitter thereon on a chest of a subject; and
reading a value detected by said wrist sphygmomanometer with the wrist placed on the chest, wherein
the body of said wrist sphygmomanometer comprises a power supply housing unit and the cuff has an elliptical shape connected to the body via an air flow passage member and wrapped around a wrist, wherein
said body is attached to the cuff at a position corresponding to a direction of a major axis of said elliptical shape when the sphygmomanometer is fitted on the wrist,
said cuff comprises an elastic portion on a palm side of the wrist in a shape according to the wrist for appropriately fitting the sphygmomanometer on the wrist,
said wrist sphygmomanometer further comprises a heavy load portion for locating a center of gravity of said body between a center of said body and a palm side thereof, and
said heavy load portion is provided on a portion of said cuff where said elastic portion is located.

* * * * *

Adverse Decision In Interference

Patent No. 6,547,741, Kentaro Mori, Takahide Tanaka, Akira Nakagawa, Iwao Kojima, WRIST SPHYGMOMANOMETER, Interference No. 105,287, final judgment adverse to the patentees rendered, October 5, 2005, as to claims 4-6.

*(Official Gazette, February 28, 2006)*